(12) United States Patent
Yuan et al.

(10) Patent No.: US 8,460,685 B2
(45) Date of Patent: Jun. 11, 2013

(54) METHOD OF IMPROVING THE OSTEOINDUCTIVITY OF CALCIUM PHOSPHATE

(75) Inventors: Huipin Yuan, Zeist (NL); Joost Dick De Bruijn, Amersfoort (NL); Klaas De Groot, Heemstede (NL)

(73) Assignee: Progentix Orthobiology B.V., Bilthoven (NL)

( * ) Notice: Subject to any disclaimer, the term of this patent is extended or adjusted under 35 U.S.C. 154(b) by 952 days.

(21) Appl. No.: 11/919,390

(22) PCT Filed: Apr. 21, 2006

(86) PCT No.: PCT/NL2006/000210
§ 371 (c)(1),
(2), (4) Date: Aug. 31, 2009

(87) PCT Pub. No.: WO2006/115398
PCT Pub. Date: Nov. 2, 2006

(65) Prior Publication Data
US 2010/0003304 A1 Jan. 7, 2010

Related U.S. Application Data

(60) Provisional application No. 60/674,222, filed on Apr. 22, 2005.

(30) Foreign Application Priority Data

Apr. 25, 2005 (EP) .................................... 05075973

(51) Int. Cl.
*A61K 9/00* (2006.01)
*A61K 33/06* (2006.01)
*A01N 59/26* (2006.01)

(52) U.S. Cl.
USPC .......... 424/400; 424/422; 424/93.1; 424/600; 424/617; 424/673

(58) Field of Classification Search
USPC ................ 424/400, 422, 93.1, 600, 617, 673
See application file for complete search history.

(56) References Cited

U.S. PATENT DOCUMENTS

| | | | |
|---|---|---|---|
| 5,525,148 A | 6/1996 | Chow et al. | |
| 5,534,244 A | 7/1996 | Tung | |
| 7,419,680 B2 * | 9/2008 | LeGeros | 424/423 |
| 2002/0107570 A1 * | 8/2002 | Sybert et al. | 623/13.17 |

FOREIGN PATENT DOCUMENTS

WO   WO-2005/032466   4/2005

OTHER PUBLICATIONS

Harrison et al., Biomaterials (2004) 25:4977-4986.
International Search Report for PCT/NL2006/000210, date mailed on Aug. 17, 2006, 4 pages.

* cited by examiner

*Primary Examiner* — Ruth Davis
(74) *Attorney, Agent, or Firm* — Morrison & Foerster LLP

(57) ABSTRACT

The invention relates to methods of improving the osteoinductivity of calcium phosphate materials, to calcium phosphate materials having improved osteoinductivity as well as bone (re)generation scaffolds produced therefrom and to the use of such materials and scaffolds in methods of treatment.

11 Claims, 4 Drawing Sheets

METHOD OF IMPROVING THE OSTEOINDUCTIVITY OF CALCIUM PHOSPHATE

CROSS-REFERENCE TO RELATED APPLICATIONS

This application is a National Phase filing under 35 U.S.C. §371 of International Application No. PCT/NL2006/000210 filed on Apr. 21, 2006, which claims the benefit of European Patent Application No. 05075973.7, filed Apr. 25, 2005 and U.S. Provisional Application Ser. No. 60/674,222, filed Apr. 25, 2005, all of which are hereby incorporated herein by reference in their entirety.

FIELD OF THE INVENTION

The invention relates to methods of improving the osteoinductivity of calcium phosphate materials, to calcium phosphate materials having improved osteoinductivity as well as bone (re)generation scaffolds produced therefrom and to the use of such materials and scaffolds in methods of treatment.

BACKGROUND OF THE INVENTION

Certain subclasses of calcium phosphates, specifically those which comprise specific arrangements of surface microporosity and micro-architecture have been described as being osteoinductive, which term refers to the ability of materials to induce bone cell growth and thus to initiate new bone formation in non-osseous tissue. The formation of such bone includes attachment and aggregation as well as proliferation and differentiation of cells on the material surface, followed by bone matrix formation on the material surface, bone mineralization and bone remodelling to form mature bone. The osteoinductive potential of calcium phosphate materials varies, as indicated by the earliest time for bone formation to occur and the amount of the induced bone.

When an osteoinductive calcium phosphate material is used as in implant material during surgical repair of bone defects, new bone is formed both by osteoconduction near the existing bone as well as by osteoinduction far from the existing bone. Meanwhile the osteoinductive calcium phosphate material would enhance osteoconductive bone formation since it concentrates growth factors and attracts bone-forming cells. Therefore the use of osteoinductive calcium phosphate materials in bone repair results in bone formation starting earlier, in bone formation at increased amounts and in bone formation far from the existing bone as compared to non-osteoinductive calcium phosphate materials. In general, the higher osteoinductive potential of the material, the more effective procedures aimed at repairing bone defects can be performed. Therefore there exists an ongoing need for improving the osteoinductivity of resorbable calcium phosphate materials.

SUMMARY OF THE INVENTION

The present inventors have found that the osteoinductivity of calcium phosphate materials may be considerably improved by providing the calcium phosphate material with an effective amount of trace elements, which trace elements are then released over time from the material. In essence, the material must be capable of release of the trace elements for the osteoinductive capacity to be effectively improved. Therefore a very suitable calcium phosphate material and one that inherently exhibits the ability for release of trace elements is a resorbable calcium phosphate material, because such a material is capable of releasing trace elements comprised therein while it is being degraded and resorbed.

In a first aspect, the present invention provides a method of improving the osteoinductivity of a calcium phosphate material comprising providing the calcium phosphate material with an effective amount of trace elements wherein said material is capable of release of said trace elements.

Preferably, the calcium phosphate material draws its capacity of release of said trace elements from the fact that it is resorbable. Thus, in one preferred embodiment, the present invention relates to a method of improving the osteoinductivity of a calcium phosphate material comprising providing a resorbable calcium phosphate material with an effective amount of trace elements.

In another preferred embodiment, the calcium phosphate material is in the form of a ceramic, a cement or a coating of calcium phosphate or has the form of a calcium phosphate-containing glass or composite. Preferably, the calcium phosphate ceramic is resorbable biphasic calcium phosphate (BCP) or resorbable tri-calcium phosphate (TCP), most preferably resorbable TCP. The calcium phosphate material is preferably porous and more preferably has pore sizes large enough to permit invasion of the material by bone forming cells.

In yet another preferred embodiment, the trace element is selected from the group consisting of water soluble salts of F, Si, Cu, Li, Al, Mg, Mn, Zn, Ge, Sr and combinations thereof. More preferably the trace element is a water soluble salt of F and/or Li, most preferably the sodium salt of F and/or chloride salt of Li.

The present invention provides in another aspect a calcium phosphate material for use in a bone (re)generation scaffold, wherein the material comprises an effective amount of trace elements and is capable of release of said trace elements. Again, the calcium phosphate material preferably draws its capacity of release of said trace elements fro the fact that it is resorbable. Therefore, in a preferred embodiment, the present invention relates to a resorbable calcium phosphate material for use in a bone (re)generation scaffold, wherein the material comprises an effective amount of trace elements.

A calcium phosphate material according to the invention has important utility in or as a bone (re)generation scaffold and the present invention therefore also relates to a bone (re)generation scaffold comprising a calcium phosphate material according to the invention. Also in this aspect, the calcium phosphate material is preferably resorbable, and preferably in the form of a ceramic, a cement or a coating of calcium phosphate or in the form of a calcium phosphate-containing glass or composite, and the calcium phosphate ceramic is preferably resorbable biphasic calcium phosphate (BCP) or resorbable tri-calcium phosphate (TCP), most preferably TCP. The trace element is preferably selected from the group consisting of water soluble salts of F, Si, Cu, Li, Al, Mg, Mn, Zn, Ge, Sr and combinations thereof, more preferably selected from a water soluble salt of F and Li, most preferably selected from the sodium salt of F and chloride salt of Li.

In a preferred embodiment, the bone (re)generation scaffold further comprising stem cells, osteogenic cells, and/or osteoprogenitor cells.

In still a further aspect, the present invention provides a method of accelerating bone formation at an implanted tissue (re)generation scaffold, comprising providing as a material comprised in said scaffold a calcium phosphate material of the invention.

In still a further aspect, the present invention provides a method of regenerating bone in a subject in need thereof, comprising providing the subject with a bone (re)generation scaffold according to the invention.

In still a further aspect, the present invention provides the use of a resorbable calcium phosphate material according to the invention for the manufacture of a medicament for repairing an osseous defect.

In still a further aspect, the present invention provides the use of water soluble salts of trace elements for improving the osteoinductivity of a calcium phosphate material, preferably an osteoinductive calcium phosphate material, more preferably a resorbable and osteoinductive calcium phosphate material.

DETAILED DESCRIPTION OF THE INVENTION

Definitions

Figure 1:
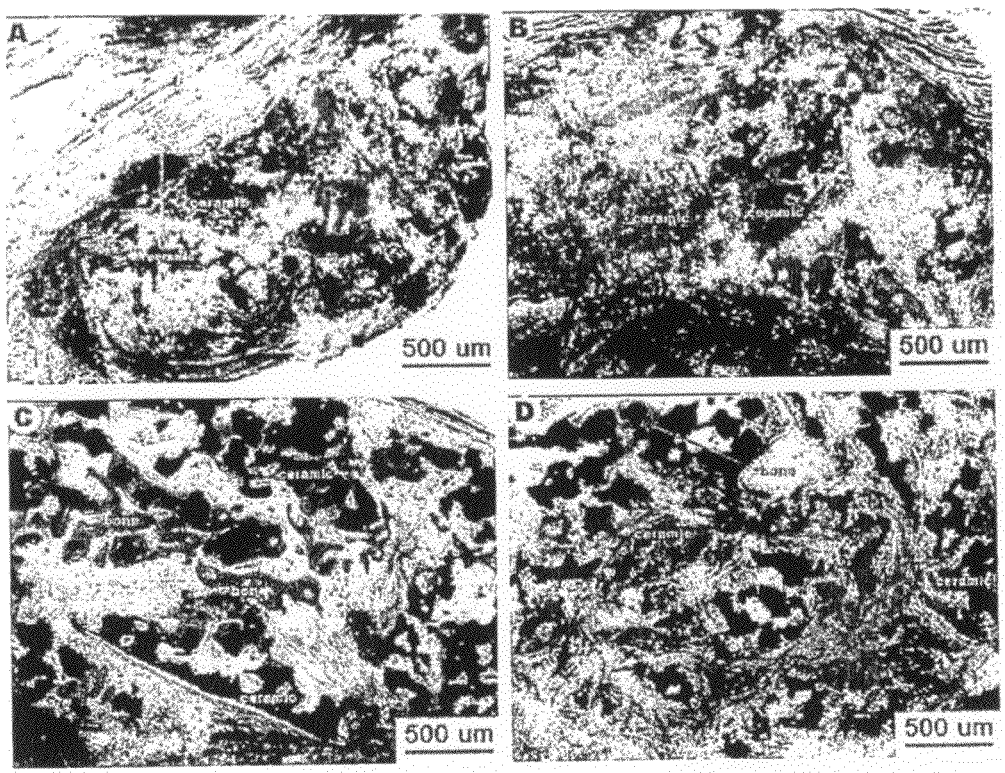
FIG. 1 shows micrographs demonstrating the influence of sodium fluoride on the osteoinductive potential of tri-calcium phosphate ceramic (TCP) in a dose-dependent manner (implants of 1.0 cc particles having particle size of 1-3 mm, 12 weeks after intramuscular implantation in goats, non-decalcified section, methylene blue and basic fuchsin staining as described in Example 1). Panel A shows limited bone induction by TCP alone; Panel B shows slightly enhanced bone induction by TCP containing 8 mmol NaF/100 g TCP; Panel C shows considerably enhanced bone induction by TCP containing 16 mM NaF/100 g TCP; Panel D shows limited enhancement of bone induction by TCP containing 24 mmol NaF/100 g TCP.

The term "resorbable osteoinductive calcium phosphate material" as used herein refers to an osteoinductive calcium phosphate material that exhibits chemical dissolution and cell-mediated resorption when placed in a mammalian body, and most importantly an osteoinductive calcium phosphate material gives bone formation in non-osseous sites.

The term "an effective amount of trace elements" as used herein refers to an amount of trace elements comprised in or provided to the material that is low enough to avoid any toxic effects of the trace elements to the bone-forming cells, while at the same time the amount is high enough to have the desired effect of providing improved osteoinductivity to the calcium phosphate. The skilled person is well aware of the various methods available for assessing or determining the effective amount for each trace element in accordance with this definition, for instance by determining a concentration-response profile for that trace element. A suitable method for NaF and LiCl is for instance provided in the Examples below (Examples 1 and 2).

The present invention is based on the finding that trace elements have the ability to improve the osteoinductivity and thereby the osteogenic capacity of calcium phosphates. In particular such trace elements are contemplated that have an effect on or that influence bone metabolism.

Without wishing to be bound by theory it is believed that the improvement of the osteoinductivity of calcium phosphate materials as contemplated by the present invention is based on the fact that the ions that are released with resorption (or degradation) from the calcium phosphate material they have an advantageous effect on the bone forming process either by advantageously affecting cell aggregation, cell proliferation, or cell differentiation or cellular metabolism, or advantageously affect bone mineralization or remodelling of bone. The result of these advantageous effects is that bone is formed earlier, faster and to a larger extent (more bone is formed). Hence, the introduction of trace elements, preferably those that influence bone metabolism, into osteoinductive calcium phosphate materials improves on one hand the osteoinductive potential of the calcium phosphate material and causes more rapid and more elaborate bone formation in ectopic sites, and on the other hand results in more effective bone repair in orthopaedic sites.

The effective amount of a trace element depends both on the trace element and on the calcium phosphate used. For instance in the case of sodium fluoride (NaF) and TCP, an effective amount is in the range of 8-24 mmol, NaF/100 g with an optimum around 16 mmol NaF/100 g TCP. Therefore, a preferred range for NaF in the case of TCP is 10-22, more preferably 12-20, still more preferably 14-18, still more preferably 15-17, and most preferably around 16 mmol NaF/100 g TCP. While for LiCl, an effective amount is in the range of 5-45 mmol, LiCl/100 g with an optimum around 15 mmol LiCl/100 g TCP. Therefore, a preferred range for LiCl in the case of TCP is 10-22, more preferably 12-20 mmol/100 g.

It should be taken into account that the toxicity of trace elements depends on the concentration in the body or in parts thereof. Therefore, the effective amount that can be comprised in a calcium phosphate material before it becomes toxic depends in many cases on the rate of release and thus on the stability of the calcium phosphate matrix in the body. Less stable calcium phosphate matrices will degrade more rapidly, releasing larger amounts of trace elements per unit of time and can hold lower effective amounts of trace elements than do more stable matrices. An advantage in the case of ceramics, comprising ratios of compounds With different stability, is that the stability of the ceramic can be varied by varying the amounts of the various compounds. This allows for adjustment of the desired release-rates of trace elements from the calcium phosphate material.

A method of improving the osteoinductivity of a calcium phosphate material according to the present invention is in particular aimed at improving the osteoinductive potential and thereafter the osteogenic capacity of calcium phosphate materials. Such calcium phosphate materials with improved osteogenic capacity can be used alone, as carriers of growth factors, as carriers of genes and as scaffolds of bone tissue engineering for repair, augmentation and replacement of bone tissue.

The method comprises providing the calcium phosphate material with an effective amount of trace elements.

In choosing a suitable calcium phosphate for applying the method of the invention, preference insofar as repair of bone defects is concerned would go to an osteoinductive calcium phosphate, however, this is no essential requirement as the osteoinductivity of calcium phosphates having low osteoinductive potential may be improved by the present invention. However, osteoinductivity of surgical implants is preferably as high as possible and osteoinductive calcium phosphate material are therefore preferred. Although most calcium phosphates are osteoinductive to a certain extent, specifically those which comprise specific arrangements of surface microporosity and micro-architecture have been described as being osteoinductive. Calcium phosphate materials having such physical characteristics are therefore preferred. Chemically, the calcium phosphate is preferably biphasic calcium phosphate (BCP) or tri-calcium phosphate (TCP), more preferably TCP.

The present invention in a preferred embodiment contemplates the improvement of the osteoinductivity of resorbable calcium phosphates. The preference for this particular calcium phosphate material resides in its inherent capacity of release of a water soluble trace element comprised in the material during the resorption of the calcium phosphate by its environment.

The (bio-)resorbability of calcium phosphate materials appears to be dependent on their chemical/crystal composition, their structure as "materials", and on the environment at the implantation site. The existence of two different biologic resorption pathways was proposed: one involving solution-mediated (chemical) processes (implant solubility in physiologic solutions) and the second involving cell-mediated processes (phagocytosis). Contrary to expectations, the material more closely resembling the body's own hard tissue component, the hydroxyapatite, was found to dissolve much more slowly than the tri-calcium phosphates not naturally occurring in bone if similar ceramic structures and similar degrees of purity were used. It can be stated that high density implants of crystalline HA have lesser tendency to resorb because of their chemistry and their small surface area. Dense tri-calcium phosphate implants exhibit a measurable dissolution rate. Porous ceramics of β-TCP generally seem to (bio)degrade much more rapidly (degrade at higher rate) than do ceramics made of HA. Furthermore tri-calcium phosphate implants resorb much more rapidly than tetra calcium phosphate implants of similar structure.

For aspects of the present invention release or liberation of trace elements from the calcium phosphate matrix is preferably contemplated to continue for a period of between 1 day and 1 year, more preferably for a period of between 1 to 20 weeks, even more preferably for a period of between 4 to 8 weeks. In the case of a resorbable calcium phosphate material, the calcium phosphate material is fully resorbed within that time period, or the trace elements are otherwise fully liberated from the material as a result of the degradation. The release may be in the form of a so-called sustained (or controlled) release, whereby the trace elements are released steadily from the material over a prolonged period of time, thus reducing the dosage liberated at any one time and realizing an essentially continuous slow release. The release my also me an intermitted release, for instance accomplished by providing the trace elements in concentrated "pockets" in the calcium phosphate material. Alternatively, the release may be a burst release, wherein the trace elements are essentially released over a short period of time in high concentration. Of all forms of release, sustained release is preferred.

Preferably, trace element used in aspects of the present invention are selected from the group consisting of F, Si, Cu, Li, Al, Mg, Mn, Zh, Ge, Sr and combinations thereof. More preferably the trace elements are F and/or Li.

The trace elements employed in methods of the invention or comprised in the calcium phosphates of the invention are preferably in water-soluble form, i.e. as a water-soluble salt. This has the advantage that upon their release from the calcium phosphate matrix they can exert their effect on the bone-forming process in ionic form. In principal any counter ion can be used in such water-soluble salts. In the case of F, the water-soluble salt is preferably provided as NaF and in the case of Li, the water-soluble salt is LiCl.

The provision of an effective amount of trace elements to a calcium phosphate material capable of release of said trace elements may be performed by pre-mixing trace elements and ingredient for the calcium phosphate material and forming the mixture into the calcium phosphate material and/or scaffold of the invention.

For instance, a calcium phosphate ceramic comprising trace elements may be prepared by mixing together calcium phosphate powder (e.g. TCP powder);
1.0-2.0% of $H_2O_2$ in an aqueous solution containing trace elements (in an amount sufficient to yield the effective amount of trace elements in the end product) in a ratio of about 100-150 ml of aqueous solution per 100 g of calcium phosphate powder, and
naphthalene particles (500-1400 μm) in a ratio of about 30-50 g of naphthalene particles per 100 g of calcium phosphate powder, and foaming the mixture at 50-70° C. to yield porous green bodies. After drying, the naphthalene can be evaporated at 80-100° C. and the green bodies can be sintered at 1100° C. for 8 hours. The ceramic may then be formed in any shape or form, for instance in the form of particles (1.0-3.0 mm), which may then be cleaned, for instance ultrasonically with acetone, ethanol and water, after which they may be dried at 80° C.

Alternatively, the calcium phosphate material may be ready-made and loaded with the trace elements, for instance by soaking the calcium phosphate material man aqueous solution of the trace elements, optionally followed by drying of the thus impregnated calcium phosphate material.

Thus, the trace elements may be loaded into a ready-made calcium phosphate material by soaking or may be incorporated into a calcium phosphate material during the fabrication thereof by pre-mixing ingredients. Preferably, a method of improving the osteoinductivity of a calcium phosphate material encompasses the pre-mixing of the ingredients before fabrication of the calcium phosphate material.

In principle, the calcium phosphate material in aspects of the present invention may have any shape or form. For instance it may be in the form of blocks, foams, sponges, granules, cements, implant coatings, composite components. For instance it may be in the form of a calcium phosphate-containing glass or composite. The term "calcium phosphate-containing composite" is meant herein to refer to a polymeric material containing calcium phosphate. The material may for instance be combined organic/inorganic materials or ceramics and may be from various origins, natural, biological or synthetic. The various forms may for instance be obtained by extrusion, injection moulding, solvent casting, particular leaching methods, compression moulding and rapid prototyping such as 3D Printing, Multi-phase Jet Solidification, and Fused Deposition Modeling (FDM) of the materials. The choice for a particular material is of course dependent on the application that is foreseen.

A suitable cement may for instance be used as a injectable (bone) scaffold material and may upon hardening be loaded with cells. Such a cement may for instance comprise hydroxy apatite (HA) microparticles that, depending on their manufacturing method, may either be dense or microporous. A suitable particle size is one in which the particles have a diameter in the range of 10-1000 µm, preferably of 200-300 µm.

The calcium phosphate material can be used as a scaffold material directly, or may be further modified or formed in a suitable scaffold material by post-production treatments such as shaping, hardening, (mold) curing, sintering, cross-linking, milling, sawing, laminating, glazing, coating, etching, impregnating or by chemically modifying its surface.

The calcium phosphate material of the invention is capable of release of the trace elements comprised in it. The term "release" as used herein refers to locally releasing in a controlled manner, i.e. in an appropriate concentration pattern over time, an effective amount of trace elements.

Release may on the one hand be achieved by selecting as the calcium phosphate a resorbable material, which inherently yields the desired result of release of trace elements from the material's matrix. On the other hand, one may choose to modify (e.g. mix, coat, impregnate) the calcium phosphate material in such a way that trace elements can be released from it, for instance in a sustained manner. Such a release system may for instance employ calcium phosphate material modified with polymeric biomaterials that may deliver trace elements by polymeric release, wherein the trace element is released from the polymer. For polymeric release, the trace element is entrapped within or adsorbed onto the calcium phosphate material by a polymeric release coat material and released at the site of the implant, with release typically may occur through a combination of surface desorption, diffusion and polymer degradation. The polymeric release coat material may for instance (slowly) dissolve at the site of implantation to release the trace elements from the calcium phosphate material. Polymeric release coat material may be any material suitable for the adsorption of trace elements, preferably trace elements selected from the group consisting of F, Si, Cu, Li, Al, Mg, Mn, Zn, Ge, Sr and combinations thereof, more preferably F and Li. Materials having an ion-exchange capacity and capable of ion release are very suitable as polymeric release coat material.

The scaffold, in turn, may be prepared entirely from a calcium phosphate material or may consist of a core comprise a coating with an (optionally modified) calcium phosphate material. The calcium phosphate material may in turn comprise polymers capable of controlled release of trace elements and the polymers may take the form of a coating loaded with trace elements, said coating being capable of locally releasing in a controlled manner an effective amount of trace elements.

As stated, release of trace elements from the calcium phosphate material or from a polymeric material comprised therein may occur through surface desorption, diffusion, and/or material degradation, or a combination of these of either the trace element-releasing polymer or the resorbable calcium phosphate material. For this purpose, the calcium phosphate material may comprise a variety of natural and synthetic polymers suitable for release of trace elements, which can be categorized as either hydrophobic [e.g., poly(lactide-co-glycolide) (PLG), polyanhydrides] or hydrophilic polymers [e.g., hyaluronic acid (HA), collagen, polyethylene glycol) (PEG)]. Synthetic polymers such as PLG and polyanhydrides are very suitable for controlled release of trace elements according to the present invention, as they are biocompatible and available in a range of copolymer ratios to control their degradation.

The calcium phosphate material may further comprise cytokines and growth factors capable of supporting the osteogenic nature of the material.

Suitable cytokines and growth factors include epidermal growth factor (EGF), fibroblast growth factors (bFGF, FGF-1, and FGF-2), interferon-(IFN-), interleukins (IL-1, IL-4, IL-6, IL-10, and IL-11), platelet-derived growth factor-(PDGF), transforming growth factors (TGF- and TGF-$\beta$), tumor necrosis factor-(TNF-), insulin-like growth factors (IGF-I and IGF-II), osteoclast differentiation factor (ODF, also known as OPGL [osteoprotegerin ligand], RANKL [receptor activator of NFB ligand], and TRANCE [TNF-related activation-induced cytokine]), and macrophage colony-stimulating factor (M-CSF). Most of these, such as IL-1, IL-4, IL-6, IL-11, TNF, EGF, bFGF, FGF-2, PDGF, and M-CSF stimulate bone resorption. Some, such as IGF-I and IGF-II, FGF-2, and TGF-3 enhance bone formation, while others (PDGF and TGF-$\beta$) also stimulate proliferation and differentiation of collagen-synthesizing cells (Watkins B A, Li Y, Lippman H E, Seifert M F (2001) Omega-3 Polyunsaturated Fatty Acids and Skeletal Health. Experimental Biology and Medicine 226:485-97). Preferred growth factors include BMP, IGF, PTH and PDGF.

Alternatively, in case that a bone (re)generation scaffold according to the invention is to be provided with stem cells, osteogenic cells, and/or osteoprogenitor cells, such cells may carry genes that stimulate bone-formation, such as genes for BMP.

The bone (re)generation scaffold or bioactive material may further comprise demineralised bone matrix (DBM) and/or mineralized bone particles as known in the art.

The method of accelerating bone formation at an implanted tissue (re)generation scaffold according to the present invention, comprises the provision of a calcium phosphate material according to the invention as a scaffold material and effecting release of trace elements comprised therein. Release of trace elements can be affected as described above, for instance by allowing the degradation of the scaffold material at the site of implantation. Normally, chemical dissolution and cellular degradation will result in degradation of resorbable materials over time. Alternatively, and for calcium phosphate materials which are more stable, or resorb only very slowly under in vivo conditions, degradation of the parts of the calcium phosphate material that comprise the trace elements may be enhanced so as to achieve the release of the trace elements. Enhancement may for instance be accomplished by providing the calcium phosphate with a higher amount of TCP or generally by providing a material with a higher rate of degradation. Alternatively, the composition of the calcium phosphate material may be modified such that the material is capable of being loaded with trace elements and thereafter, once implanted, is capable of releasing the trace elements, for instance by polymeric release.

The method of (re)generating bone in a subject in need thereof, comprises the step of providing the subject with a bone (re)generation scaffold according to the invention. The scaffold will generally be implanted by surgery. The surgical procedures to implant the scaffold may be similar to the procedures that are normally used by the skilled surgeon when implanting other types of scaffolds.

By way of example, and not of limitation, Examples of the present invention will now be given.

EXAMPLES

Example 1

Improving Osteoinductive Potential of Resorbable Osteoinductive Tri-Calcium Phosphate Ceramic with Sodium Fluoride 1.1 Materials and Methods
1.1.1 Preparation of the Materials
Tri-Calcium Phosphate Ceramic.

TCP powder (Plasma Biotal UK) was mixed with $H_2O_2$ solution (1.0-2.0% in water, 100-150 ml/100 g TCP powder) and naphthalene particles (500-1400 μm, 30-50 g/100 g powder), and foamed at 50-70° C. to get porous green bodies. After drying and evaporation of naphthalene at 80-100° C., the green bodies were sintered at 1100° C. for 8 hours. Ceramic particles (1.0-3.0 mm) were prepared by mortar grinding and sieving and cleaned ultrasonically with acetone, ethanol and water, and finally dried at 80° C.

Tri-Calcium Phosphate Ceramics with Sodium Fluoride.

The same procedure was used to prepare TCP ceramics with sodium fluoride by dissolving sodium fluoride in the $H_2O_2$ solution used for preparing the TCP ceramic itself (for amounts see Table 1).

TABLE 1

Preparation of TCP ceramics containing Sodium Fluoride

|  | TCP | 8 mmol NaF/100 g TCP | 16 mmol NaF/100 g TCP | 24 mmol NaF/100 g TCP |
|---|---|---|---|---|
| TCP powder | 100 g | 100 g | 100 g | 100 g |
| $H_2O_2$ | 100-150 ml | 100-150 ml | 100-150 ml | 100-150 ml |
| NaF in $H_2O_2$ | 0 | 0.34 g | 0.68 g | 1.02 g |

1.1.2. Animal Study

The osteoinductive potential of sodium fluoride-loaded TCP ceramic was tested in a pilot study in muscles of goats. After sterilization (autoclaving at 121° C. for 30 minutes), a volume of 1.0 cc of 1-3 mm ceramic particles (granules) of each TCP-only, TCP with 8 mmol NaF/100 g, TCP with 16 mmol NaF/100 g and TCP with 24 mmol NaF/100 g were implanted in dorsal muscles of 4 goats for 12 weeks (total 4 implants in each of 4 goats).

1.1.3. Histology

Twelve weeks after implantation the animals were sacrificed and the implants were harvested with surrounding tissues and fixed in 1.5% glutaraldehyde in 0.14M cacodylate buffer. The fixed samples were dehydrated in a graded series of aqueous ethanol solutions (70%, 80%, 90%, 96% and 100%×2) and finally embedded in methyl methacrylate (MMA). Using standard procedures non-decalcified sections (10-20 μm) were made and stained with methylene blue and basic fuchsin for histological observation and histomorphometrical analysis regarding bone formation.

1.1.4. Histomorphometry

Histomorphometry was performed on the sections across the middle of the implants and to the percentage of the formed bone in the available space was measured using image analysis.

1.2. Results

The volume of the implants as determined by their overall size had decreased to less than 1 cc after intramuscular implantation in goat muscle for 12 weeks, indicating that the TCP material, optionally loaded with different concentration of sodium fluoride, was resorbed. Resorption of the materials was also observed histologically. Using microscopy, it appeared that TCP was indeed largely resorbed, and that only residual amounts of TCP Were in fact harvested from the animals. Most of the porous TCP ceramic particles had fragmented into smaller particles as seen in histological sections. Resorption of TCP loaded with sodium fluoride was seen as well, but the implanted ceramic particles were more intact.

Figure 2:
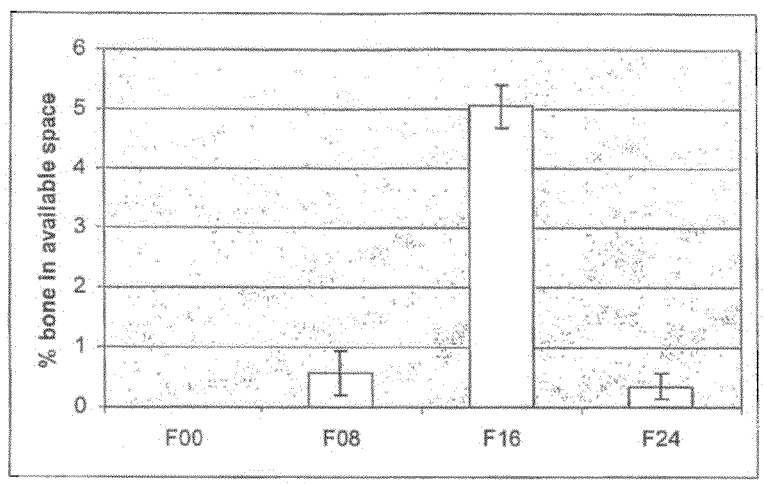
FIG. 2 shows bar graphs indicating the dose-dependent influence of NaF on the percentage of bone in the available space of the implants as determined by bistomorphometrical methods described in Example 1: In F00 (implants of TCP-only ceramic alone) bone can be histologically observed but the amount of bone formed is limited and too little to be measured quantitatively. In F08 (TCP containing 8 mmol NaF/100 g), more bone was formed in the implants but the amount of the formed bone in the available space (the void formed by the pores in the particles and the void in between the ceramic particles that is accessible to bone forming cells) is less than 1%. 5% bone was formed in the available space of F16 (TCP containing 16 mmol NaF/100 g). Using even higher concentrations of NaF as shown in F24 (TCP containing 24 mmol NaF/100 g), again less than 1% bone was formed.

TCP-only (not loaded with NaF) gave bone formation in 2 out of 4 goats. In these 2 goats that gave bone formation in TCP-only implants, even more bone was found in TCP loaded with sodium fluoride. Meanwhile more bone was formed in TCP with 16 mmol NaF/100 gTCP than in TCP with 8 mmol NaF/100 g TCP and 24 mmol NaF/100 g TCP (see FIGS. 1 and 2).

1.3. Discussion and Conclusion

The ability to give bone formation in non-osseous tissues varies individually with goats, but the results herein show that once the resorbable TCP gives bone formation in muscles of goats, the bone formation is further improved by sodium fluoride at certain concentration (16 mmol NaF/100 g TCP in this study). Improving of osteoinductive potentials with sodium fluoride as shown in the study provides the approach to improve the osteoinductive potentials and thereafter the osteogenic capacities of resorbable calcium phosphate materials with trace elements having positive influence on bone metabolism.

Example 2

Improving Osteoinductive Potential of Resorbable Osteoinductive Tri-Calcium Phosphate Ceramic with Lithium Chloride 2.1. Materials and Methods
2.1.1. Preparation of the Materials
Tri-Calcium Phosphate Ceramic.

TCP powder (Plasma Biotal, UK) was mixed with $H_2O_2$ solution (1.0-2.0% in water, 100-150 ml/100 g TCP powder) and naphthalene particles (500-1400 μm, 30-50 g/100 g powder), and foamed at 50-70° C. to get porous green bodies. After drying and evaporation of naphthalene at 80-100° C., the green bodies were sintered at 1100° C. for 8 hours. Ceramic particles (1.0-3.0 mm) were prepared as described above and cleaned ultrasonically with acetone, ethanol and water, and finally dried at 80° C.

Tri-Calcium Phosphate Ceramics with Lithium Chloride.

The same procedure was used to prepare TCP ceramics with lithium chloride by dissolving lithium chloride in the $H_2O_2$ solutions used for preparing the TCP ceramic itself (for amounts see Table 2).

TABLE 2

Preparation of TCP ceramics containing Lithium Chloride

|  | TCP | 5 mmol LiCl/100 g TCP | 15 mmol LiCl/100 g TCP | 45 mmol LiCl/100 g TCP |
|---|---|---|---|---|
| TCP powder | 100 g | 100 g | 100 g | 100 g |
| $H_2O_2$ | 100-150 ml | 100-150 ml | 100-150 ml | 100-150 ml |
| LiCl in $H_2O_2$ | 0 | 0.21 g | 0.63 g | 1.90 g |

2.1.2. Animal Study

The osteoinductive potential of TCP ceramic loaded with lithium chloride was tested in a pilot study in muscle of goats. After sterilization (autoclaving at 121° C. for 30 minutes), a volume of 1.0 cc of 1-3 mm ceramic particles (granules) of each TCP-only, TCP with 5 mmol LiCl/100 g, TCP with 15 mmol LiCl/100 g and TCP with 45 mmol LiCl/100 g were implanted in dorsal muscles of 4 goats for 12 weeks (total 4 implants in each of 4 goats).

2.1.3. Histology

Twelve weeks after implantation the animals Were sacrificed and the implants were harvested with surrounding tissues and fixed in 1.5% glutaraldehyde in 0.14M cacodylate buffer. The fixed samples were dehydrated in a graded series of aqueous ethanol solutions (70%, 80%, 90%, 96% and 100%×2) and finally embedded in MMA. Non-decalcified sections (10-20 μm) were prepared and stained with methylene blue and basic fuchsin for histological observation and histomorphometrical analysis regarding bone formation.

2.1.4. Histomorphometry

Histomorphometry was performed on the sections across the middle of the implants with regard to the percentage of the formed bone in the available space.

2.2. Results

The volume of the implants as determined by their overall size had decreased to less than 1 cc after intramuscular implantation in goats for 12 weeks, indicating the TCP material, optionally loaded with different concentration of lithium chloride were resorbed. Resorption of the materials was also observed histologically. TCP resorbed most, only a residue of TCP was harvested from the animals and most TCP ceramic broke into small particles as seen in histological sections. Resorption of TCP implemented with lithium chloride was seen as well, but more intact ceramic bodies were left.

Figure 3:
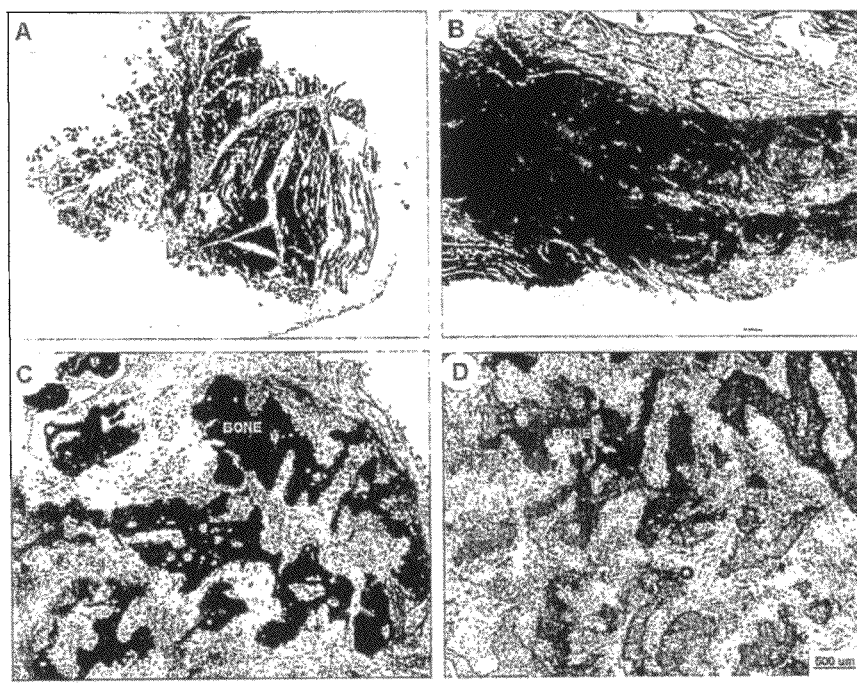
FIG. 3 shows micrographs demonstrating the influence of lithium chloride on the osteoinductive potential of tri-calcium phosphate ceramic (TCP) in a dose-dependent manner (implants of 1.0 cc particles having particle size of 1-3 mm, 12 weeks after intramuscular implantation in goats, no-decalcified section, methylene blue and basic fuchsin staining as described in Example 2). Panel A and B show the resorption of the implants of TCP(L00) and TCP with 5 mmol LiCl/100 g TCP (L05), no bone was observed; Panel C shows enhanced bone induction by TCP containing 15 mmol LiCl/100 g TCP; Panel D shows limited enhancement of bone induction by TCP containing 45 mmol LiCl/100 g TCP.
Figure 4:
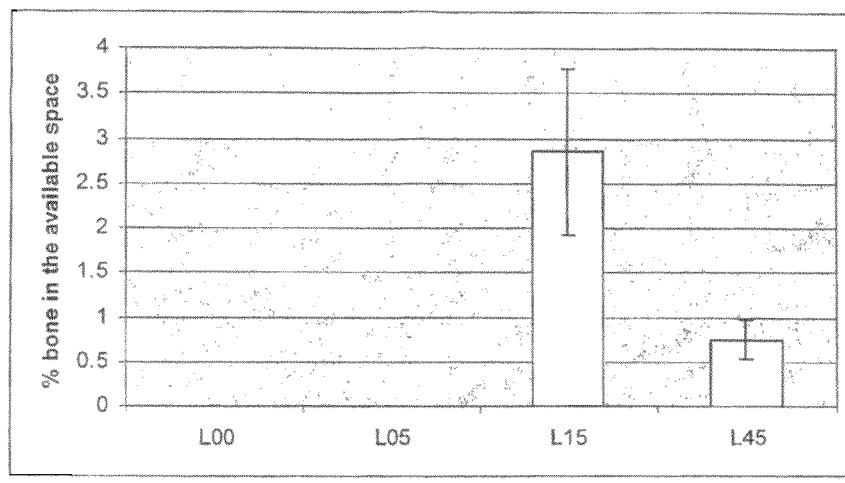
FIG. 4 shows bar graphs indicating the dose-dependent influence of lithium chloride on the percentage of bone in the available space of the implants as determined by bistomorphometrical methods described in Example 2. L00 is TCP-only implants and L05 is TCP having 5 mmol LiCl/100 g, no bone was measured. Around 3% bone Was formed in the available space of L15 which is TCP containing 15 mmol LiCl/100 g. With a higher concentration of LiCl, less than 1% bone was formed in L45 which is TCP having 45 mmol LiCl/100 g.

TCP-only gave bone formation in 2 out of 4 goats. In these 2 goats that gave bone formation in TCP-only, even more bone formation was observed in TCP loaded with 15 mmol LiCl/100 g TCP (FIGS. 3 and 4).

2.3. Discussion and Conclusion

The ability to give bone formation in non-osseous tissues varies individually with goats, but the results herein show that once bone formation can occur in muscle of goats, the bone formation is further improved by lithium chloride at certain concentration (15 mmol LiCl/100 g TCP in this study). Improving the osteoinductive potential with lithium chloride as shown in the study provides again the approach to improve the osteoinductive potentials and thereafter the osteogenic capacities of resorbable calcium phosphate materials with trace elements having positive influence on bone metabolism.

The invention claimed is:

1. A composition that consists essentially of tri-calcium phosphate (TCP) along with water-soluble salts of trace elements wherein said composition is suitable for use in a scaffold for osteoinduction of bone, wherein said composition releases said water-soluble salts of trace elements in vivo.

2. The composition of claim 1, wherein said tri-calcium phosphate is resorbable.

3. The composition of claim 1, which is in the form of a scaffold for generation or regeneration of bone.

4. The composition of claim 1, wherein said composition is in the form of a ceramic.

5. The composition of claim 1, wherein said trace element is selected from the group consisting of water soluble salts of fluorine (F), silicon (Si), copper (Cu), lithium (Li), aluminum (Al), magnesium (Mg), manganese (Mn), zinc (Zn), germanium (Ge), strontium (Sr) and combinations thereof.

6. The composition of claim 5, wherein said trace elements are F and/or Li in the form of their water soluble salts.

7. The composition of claim 1, to which has been added only the following additional component which consists of one or more bone growth factors, demineralised bone matrix (DBM) and/or mineralized bone particles.

8. A scaffold for generation or regeneration of bone comprising the composition of claim 1.

9. The scaffold of claim 8, further comprising stem cells, osteogenic cells, and/or osteoprogenitor cells.

10. A method of accelerating bone formation which method comprises implanting the scaffold of claim 8 and effecting release of trace elements comprised therein.

11. A method of generating or regenerating bone in a subject in need thereof, comprising implanting said subject with the ceramic of claim 4.

* * * * *

UNITED STATES PATENT AND TRADEMARK OFFICE
CERTIFICATE OF CORRECTION

PATENT NO. : 8,460,685 B2  
APPLICATION NO. : 11/919390  
DATED : June 11, 2013  
INVENTOR(S) : Yuan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1629 days.

Signed and Sealed this
Twelfth Day of May, 2015

Michelle K. Lee
*Director of the United States Patent and Trademark Office*